United States Patent
Keskinen et al.

(10) Patent No.: US 7,066,037 B2
(45) Date of Patent: *Jun. 27, 2006

(54) METHOD FOR MEASURING PROPERTIES OF A PARTICLE DISTRIBUTION

(75) Inventors: Jorma Keskinen, Tampere (FI); Marko Marjamäki, Tampere (FI); Mikko Moisio, Tampere (FI); Jyrki Ristimäki, Tampere (FI); Annele Virtanen, Tampere (FI)

(73) Assignee: Dekati Oy, Tampere (FI)

( * ) Notice: Subject to any disclaimer, the term of this patent is extended or adjusted under 35 U.S.C. 154(b) by 0 days.

This patent is subject to a terminal disclaimer.

(21) Appl. No.: 10/487,264

(22) PCT Filed: Aug. 20, 2002

(86) PCT No.: PCT/FI02/00683

§ 371 (c)(1),
(2), (4) Date: Jul. 22, 2004

(87) PCT Pub. No.: WO03/021236

PCT Pub. Date: Mar. 13, 2003

(65) Prior Publication Data

US 2004/0244508 A1    Dec. 9, 2004

(30) Foreign Application Priority Data

Aug. 20, 2001 (FI) .................................. 20011668

(51) Int. Cl.
*G01N 15/00*    (2006.01)
(52) U.S. Cl. .................................. 73/865.5
(58) Field of Classification Search .... 73/28.01–28.03, 73/28.05, 865.5; 324/71.4
See application file for complete search history.

(56) References Cited

U.S. PATENT DOCUMENTS

| | | | | |
|---|---|---|---|---|
| 3,763,428 A | * | 10/1973 | Preist | 324/71.1 |
| 4,117,715 A | | 10/1978 | Hoenig | 73/28.01 |
| 4,178,796 A | | 12/1979 | Zwicker et al. | 73/61.68 |
| 5,296,910 A | | 3/1994 | Cole | 356/28.5 |
| 5,576,499 A | | 11/1996 | Davies | 73/861.41 |
| 5,606,112 A | | 2/1997 | Flagan et al. | 73/28.04 |
| 5,679,907 A | * | 10/1997 | Ruck | 73/865.5 |
| 5,817,956 A | | 10/1998 | Novick | 73/865.5 |
| 5,932,795 A | | 8/1999 | Koutrakis et al. | 73/28.01 |

(Continued)

FOREIGN PATENT DOCUMENTS

DE    197 33 784 A1    2/1999

(Continued)

OTHER PUBLICATIONS

Hering et al., "On-line Determination of Particle Size and Density in the Nanometer Size Range", (1995), Aerosol Science and Technology, vol. 23, pp. 155-173.*

(Continued)

*Primary Examiner*—Hezron Williams
*Assistant Examiner*—Tamiko Bellamy
(74) *Attorney, Agent, or Firm*—Venable LLP; Eric J. Franklin

(57) ABSTRACT

A method and a device for measuring properties of a particle distribution, in which a parameter relating to the mobility of the particles is measured at one measuring point (302) and a parameter relating to the aerodynamic size of the particles is measured at a second measuring point (305). By means of the measured parameters, at least one property of the particle distribution of the original flow is determined (306).

17 Claims, 3 Drawing Sheets

U.S. PATENT DOCUMENTS 6,012,343 A     1/2000     Boulaud et al. ............ 73/865.5
6,230,572 B1     5/2001     Pui et al. ................. 73/863.21

FOREIGN PATENT DOCUMENTS

| GB | 2 344 426 A | 6/2000 |
|----|-------------|--------|
| GB | 2 346 700 A | 8/2000 |
| WO | WO 96/06341 A3 | 2/1996 |
| WO | WO 02/18910 A1 | 3/2002 |

OTHER PUBLICATIONS

Lehtimaki et al., "A Method Of Modifying The Sensitivity Function Of An Aerosol Photometer", Am. Ind. Hyg. Assoc. J. 49(8), (1998), pp. 396-400.

Keskinen et al., "Electrical Low Pressure Impactor", j. Aerosol Sci., vol. 23, No. 4, (1992), pp. 353-360.

Kelly et al., "Measurement of Particle Density By Inertial Classification of Differential Mobility Analyzer-Generated Monodisperse Aerosols", Aerosol Science and Technology 17, (1992), pp. 199-212.

Japanses Abstract, Kosaki et al., "Particle Size Distribution Measuring Device", Japanese Application No.—JP8261911 A.

* cited by examiner

METHOD FOR MEASURING PROPERTIES OF A PARTICLE DISTRIBUTION

FIELD OF THE INVENTION

The invention relates to methods and a device for measuring properties of a particle distribution.

With tightening environmental regulations, there is an increasing need for the measurement of particle emissions. In particular, the need for measurement is present in the development of filtering methods, in the research of various combustion processes, as well as in processes for monitoring actual emissions.

BACKGROUND OF THE INVENTION

For the measurement of particle emissions, various measuring devices have been developed, including for example various impactors and optical counters. The measuring devices are used to detect the particles to be analyzed and to produce information to draw up conclusions on the properties of the detected particles. In conventional impactors, in which particles with different aerodynamic dimensions are collected on different collecting substrates, information is obtained on the size distribution of the particles to be analyzed by weighing the mass of the particles collected on different collection substrates.

In more sophisticated impactors, such as an electrical low-pressure impactor, real-time electrical information is obtained on the size distribution of the particles, indicating variations in the particle distribution in real time. The electrical low-pressure impactor is described in more detail for example in the scientific article by Keskinen, Pietarinen and Lehtimäki, "Electrical low pressure impactor" published in the "Journal of Aerosol Science" [J. Aerosol Sci. Vol. 23, No. 4, pp. 353–360, 1992]. A copy of said article has been filed as an appendix to this application.

In addition to actual measuring devices, different particle classifiers are also known, including for example DMA devices (Differential Mobility Analyzer). The classifiers can be used to select from the particle flow under analysis a given subclass which is then led to the actual measuring device.

The article by W. P. Kelly and P. H. McMurry, "Measurement of Particle Density by Inertial Classification of Differential Mobility Analyzer-Generated Monodisperse Aerosol" [Aerosol Science and Technology 17:199–212, 1992], presents a method of prior art for measuring properties of a particle distribution by means of a DMA device and an impactor. FIG. 1 shows the principle of operation of this method.

In the method presented in the article, a flow 13a carrying the particle distribution to be analyzed is led to an apparatus 10 consisting of a DMA device 11 and an impactor 12. The flow is first led to the DMA device 11 which, by means of an electrical field, separates the particles with a narrow electrical range of mobility from the flow to a flow 13b to be led to the impactor 12. Particles whose electrical mobility is not within this narrow range are guided with flows 13c and 13d away from the measuring device 10.

By means of the DMA device, it has thus been possible to separate a monodispersive particle flow 13b with a given narrow electrical mobility distribution 14b from a polydispersive particle flow 13a with an electrical mobility distribution 14a led to the measuring device 10.

This monodispersive aerosol flow is then guided to the impactor 12 which subjects them to a classification based on the aerodynamic diameter. On the basis of this, it is possible to determine the aerodynamic size distribution 15 of particles contained in the flow 13b input in the impactor. When the adjustments of the DMA device 11 are known, it is possible to find out the median mobility of the monodispersive mobility distribution 14a included in the flow 13b that has passed through it.

Said article discloses how the average density of the monodispersive particle flow 13b can be determined by combining the aerodynamic size distribution 15 measured by the impactor 12 with the information on the median electrical mobility of the monodispersive particle flow 13b guided into the impactor.

The above-presented solution of prior art involves the problem that the density can only be determined for a narrow electrical mobility range at a time. In other words, by means of the method, the density can be computed for the monodispersive flow 13b selected by means of the DMA device 11. To determine the properties of a polydispersive flow 13a, this must be implemented, according to the above-presented solution of prior art, by scanning, i.e. by determining the density first in one electrical mobility range and then changing the adjustments of the DMA device in such a way that the measurement is made in another electrical mobility range. This procedure is repeated until the density has been determined in the whole range desired.

For the above-presented scanning measurement to produce reliable results, the flow 13a to be analyzed should remain unchanged during the whole measurement operation. Under real measuring conditions, there may be temporal variations in the flow to be analyzed, for which reason the above-presented solution of prior art is poorly suitable for the real-time measurement of a flow containing polydispersive particles under real conditions.

Another solution of prior art is disclosed in the article by Lehtimäki and Keskinen, "A method of modifying the sensitivity function of an aerosol photometer" published in the scientific journal "American Industrial Hygiene Association Journal" [Am. Ind. Hyg. Assoc. J 49 (8), 396–400 (1988)]. Also this article has been filed with the application. The article presents how a virtual impactor is placed in front of an optical particle counter, to separate particles with a large and a small diameter to different flows from the particle flow under analysis. From the separated flows, the flow containing large diameter particles is guided to the optical counter for the actual measurement.

Also this prior art solution involves the problem that the actual measurement operation does not relate to the actual flow to be analyzed but the flow to be analyzed has been modified before the measurement operation. Thus, it is not possible to obtain an overall conception of the properties of the particle distribution in the complete flow.

SUMMARY OF THE INVENTION

It is an aim of the method described in the present application to eliminate the above-described problems of prior art and to provide a simpler method for determining the properties of a particle distribution.

By means of the method and device of the invention, at least one property of the particle distribution is determined by measuring a parameter related to the mobility of particles at a first measuring point and a parameter related to the aerodynamic size of the particle at a second measuring point. According to the invention, at least part of the flow that has passed the first measuring point is led to the second measuring point. By means of the measured parameters, at least one property of the particle distribution contained in the original flow is determined. The property to be measured is preferably the average density of the particle distribution.

In an embodiment of the invention, the access of particles detected at the first measuring point to the second measuring point is limited for example by using, at the first measuring point, a measuring method which removes the detected particles from the flow to be analyzed. This simplifies the need for computing.

In another embodiment of the invention, a mobility channel detector and an electrical low-pressure impactor are used for measuring the parameter relating to the mobility of particles and for measuring the parameter relating to the aerodynamic size, respectively. The use of the electrical low-pressure impactor has the advantage that the whole particle size distribution, and not only a single value, can be determined simultaneously and in real time.

BRIEF DESCRIPTION OF THE DRAWINGS

In the following, the invention will be described in detail with reference to the appended drawings, in which.

DETAILED DESCRIPTION OF THE INVENTION

Figure 1:
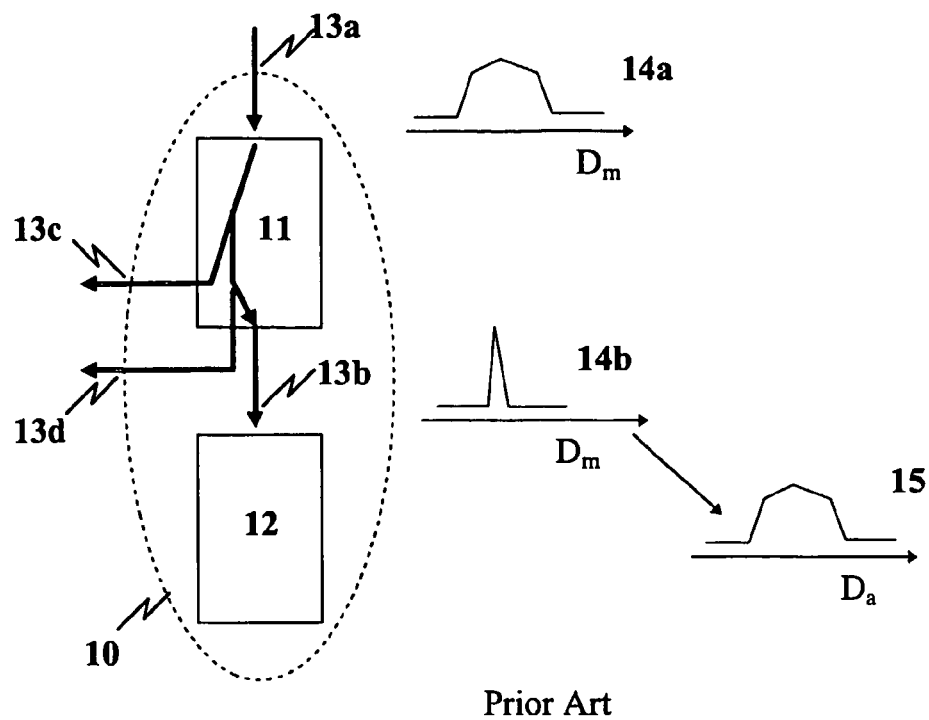
FIG. 1 shows the solution of prior art for determining the properties of a particle distribution.

FIG. 1 has been discussed above in connection with the description of prior art.

Figure 2:
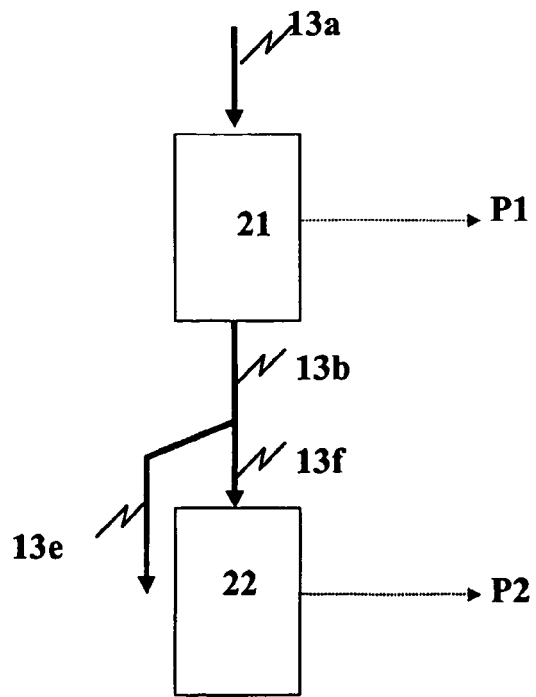
FIG. 2 shows an embodiment of the measuring device according to the invention.

FIG. 2 shows an embodiment of the measuring device according to the invention. In this embodiment, the particle distribution to be analyzed, carried by a flow 13a, is led to a first detector 21, in which at least one parameter P1 relating to the determination of a property of the particle distribution is measured from the particle distribution. The parameter P1, as well as the second parameter P2 to be described below, can be not only single variables or other single values but also a given set of values or variables. Thus, for example, a set of three different variables produced by a measurement at the measuring point to find out a parameter relating to a property of the particle distribution, can be considered one parameter in this context. In other words, said parameter P1 can preferably also be a set of parameters.

The parameter P1 preferably conveys information about the electrical or mechanical mobility of the particles. In an advantageous embodiment, the particles detected in a detector 21 are either collected in the detector or separated from the flow by other methods. The removal of the detected particles simplifies the computation to be made at a later step and makes it possible to execute a more versatile computation, particularly in cases in which the entire flow 13b to be led to the second detector 22 has passed through the first detector 21. In other words, it is advantageous in view of the method according to the invention that the flow 13b exiting the first detector 21 does not contain a significant quantity of such particles which were detected by the first detector 21.

Figure 4:
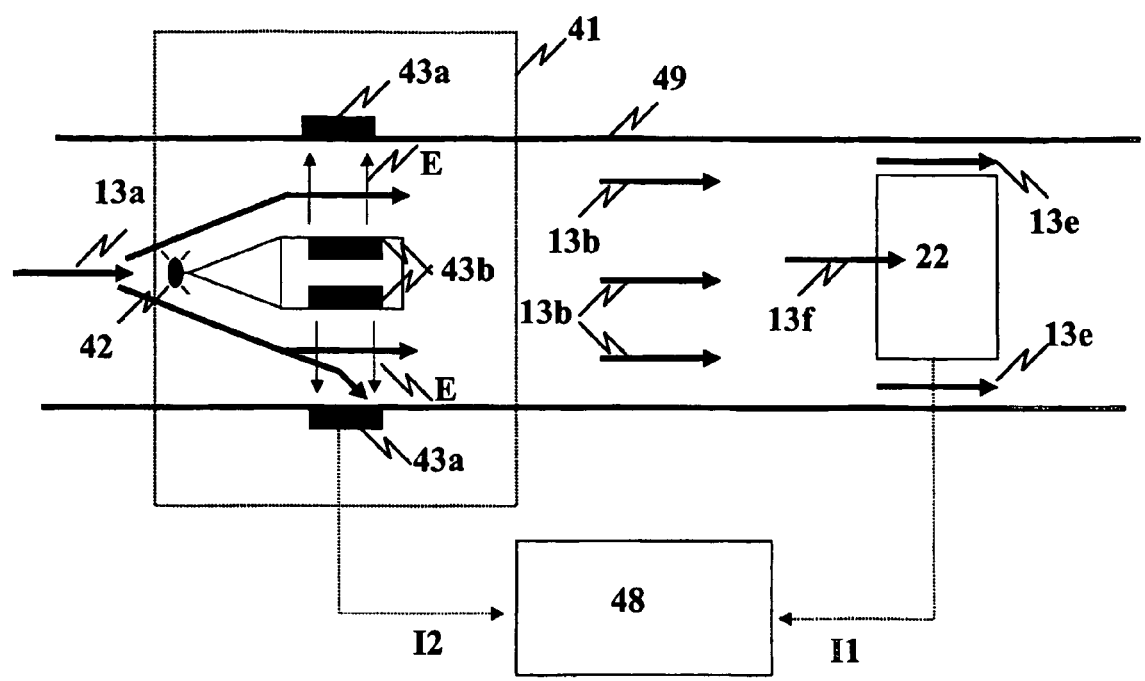
FIG. 4 shows another embodiment of the measuring device according to the invention.

The flow 13b that has passed through the first detector 21 is led to a second detector 22. Preferably, this takes place so that both measuring devices are, at least for the parts required in the detection, installed inside the same structure that guides the flow, for example a duct. FIG. 4 shows such an advantageous embodiment.

A part of the flow 13b that has passed through the first detector 21 can also be led past the second detector 22, if necessary. In FIG. 2, this is illustrated with a flow 13e. The flow 13f to be led to the second detector 22 is preferably, for the particle distribution to be analyzed, a representative sample of the flow 13b that passed through the first detector 21. Corresponding flows are also drawn in FIG. 4.

The measurement according to the invention can be made even if the flow 13f to be led to the second detector 22 did not contain a representative sample of the flow 13b coming from the first detector 21, as long as it is possible to determine the differences between the particle distribution contained in the flow 13f to be led to the second detector 22 and the flow 13a to be analyzed. Thus, the measurement according to the invention is also possible in a situation in which a part of the flow 13a to be analyzed is guided past the first detector 21 and mixed with the flow 13b that passed through the first detector 21, before the second detector 22. However, this kind of a situation is more difficult to control by computing and makes the calibration of the device more complex.

The second detector 22 generates a second measuring signal P2 relating to a property of the particle distribution. The aerodynamic size distribution of particles contained in the flow 13f guided to the second detector 22 can be preferably determined from the measuring signal P2. The properties of the particle distribution contained in the flow 13a to be analyzed can be determined by computing on the basis of the measuring signals P1 and P2 from the first and second detectors, respectively.

In an advantageous embodiment, it is possible to compare the behaviour of the second signal P2 when the first detector 21 is turned on, with a situation in which the flow to be analyzed is passed directly to the second detector 22. On the basis of such a comparison, it is possible to find out the efficiency curve of the first detector 21. Such a solution makes it possible to use simpler and less expensive detectors, but on the other hand, it will make the device less suitable for real-time measurement.

According to an advantageous embodiment of the invention, the effective density of the particle distribution to be analyzed can be computed by determining the median particle size according to the mobility size ($D_m$) as well as the median particle size according to the aerodynamic size ($D_a$). When these factors are known, the effective density can be computed from the following equation:

$$D_a\sqrt{C_a\rho_a}=D_m\sqrt{C_m\rho_{eff}}$$

In the equation, the subindex a refers to the aerodynamic size and the subindex m to the mobility size. C is Cunningham slip correction factor, $\rho_a$ is the density corresponding to the aerodynamic size, i.e. unit density (1000 kg/m$^3$), and $\rho_{eff}$ is the effective density.

In an embodiment of the invention, the above-described first detector 21 is selected so that the median particle size can be determined from the first signal P1 obtained, according to the mobility size ($D_m$), and the second detector is selected so that the median particle size can be determined from the second signal according to the aerodynamic size ($D_a$). The Cunningham slip correction factors can be determined by any way known as such for a person skilled in the art, for example by table books. Thus, the only variable remaining unknown in the above equation is the effective density of the distribution to be analyzed, wherein it can be solved.

Figure 3:
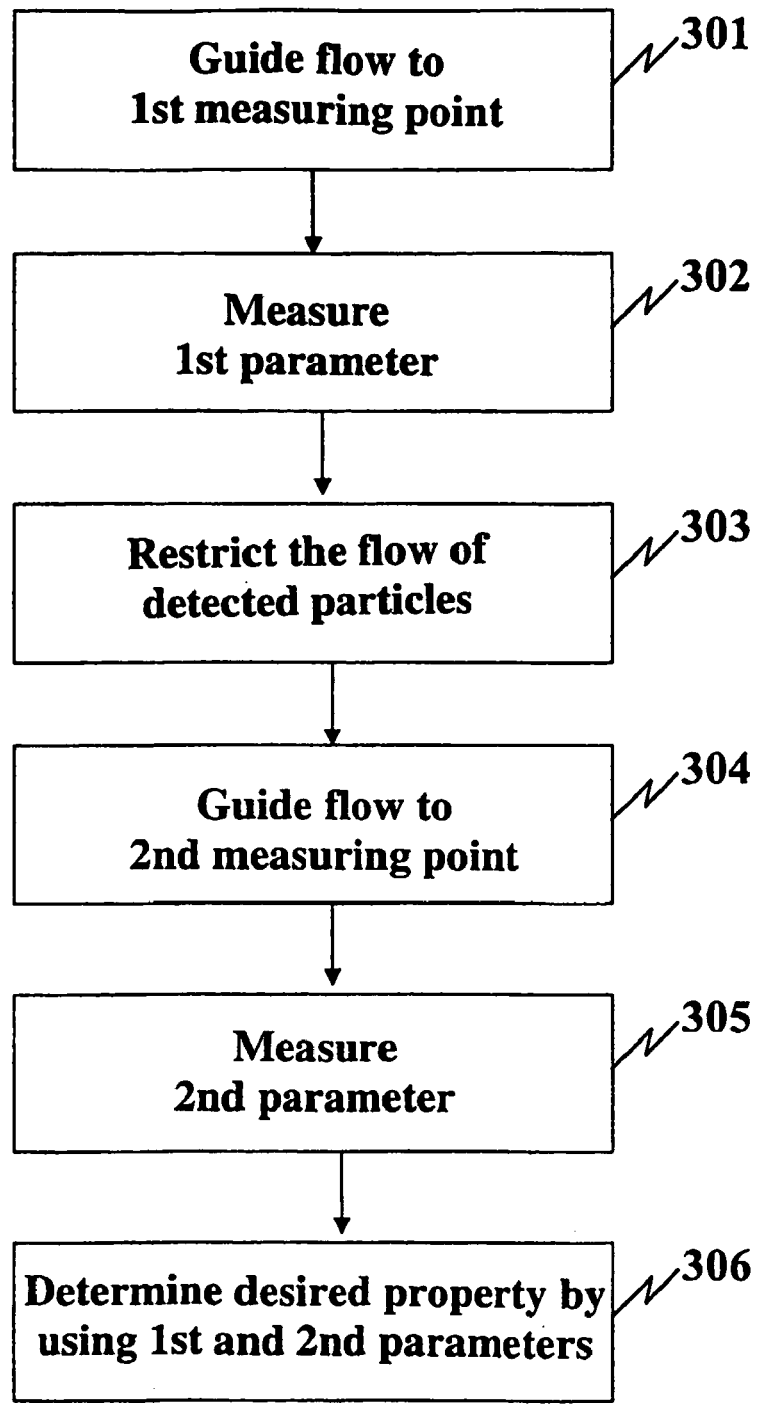
FIG. 3 shows a method according to the invention in a flow chart.

FIG. 3 shows the flow chart of a method according to the invention which implements the above-described determination of the properties of the particle distribution. In the first step 301 of the method, the flow to be analyzed is led to a first measuring point where, in step 302, the first parameter relating to the particle distribution is measured at the first measuring point. The parameter may be, for example, the magnitude I2 of an electric current output by the detector, which can be used to evaluate the median particle size according to the mobility size ($D_m$).

In step 303, the access of particles measured to the first measuring point to the second measuring point is restricted. This is preferably achieved by using a collecting method of measuring, whereby the detected particles are removed from the flow under analysis in connection with the detecting process.

In step 304, at least part of the flow that has passed through the first measuring point is led to the second measuring point, where the second parameter relating to the particle distribution is measured in step 305. The parameter may be, for example, the magnitude I1 of an electric current output by the detector, which can be used to evaluate the median particle size according to the aerodynamic size ($D_m$).

In step 306, said first and second parameters relating to the particle distribution are used to determine at least one property of the particle distribution of the original flow. To determine, for example, the effective density of the particle distribution, the above-presented formula can be preferably used.

FIG. 4 shows an embodiment of the solution according to the invention. In the figure, the flow 13a to be analyzed flows in a flue gas duct 49. The flow is first conducted through a mobility channel detector 41 installed in the flue gas duct. At first, the flow 13a passes a corona charger 42 which charges the particles in the flow 13a electrically. After this, the flow is introduced in an electric field E induced between electrodes 43a and 43b. By the effect of the electric field E, the electrically charged particles are carried with their charge to the electrode of the opposite sign. When hitting the electrode, the particle is discharged. This will cause a current I2 proportional to the electrical mobility of the particle distribution to be analyzed. Preferably, at least a significant part of the particles collected at the electrode are removed from the flow, for example by adhering to the electrode.

Furthermore, the flue gas duct 49 is provided with a second detector 22 which collects, in a way known as such, the particles that have passed through the mobility channel detector 41. When accumulating at the detector, the particles generate a current I1. Preferably, the second detector may also be, for example, an electrical low-pressure impactor of prior art. The advantage of the electrical low-pressure impactor is the fact that it can be used to measure the particle size distribution in real time, and for this reason, the above-described median particle size distribution is easy to calculate.

The current signals I1 and I2 obtained from the detectors 41 and 22 are led to a separate computing unit 48 which uses them to produce information about at least one property of the particle distribution contained in the original flow 13a.

Figure 5:
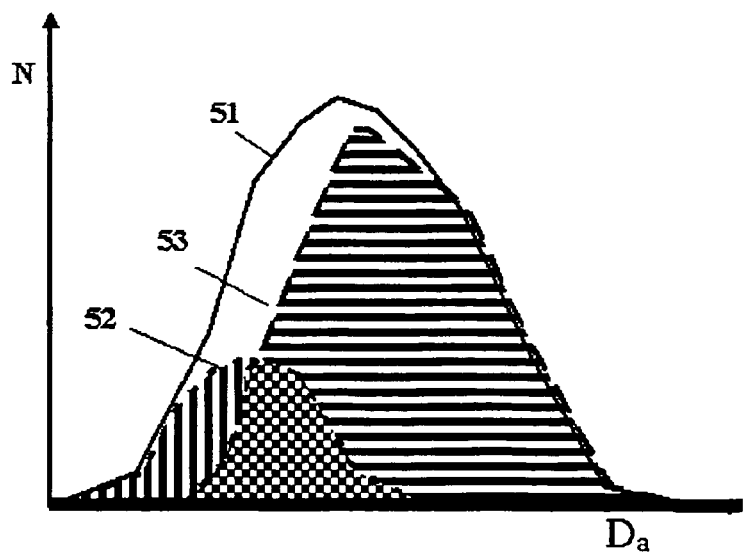
FIG. 5 illustrates the relationships between the distributions detected by different measuring devices.

FIG. 5 shows the effect of the method according to the invention on the detected particle distribution. If, in the device of FIG. 2 or 4, the second detector 22 is a detector measuring the particle size distribution, such as the above-mentioned electrical low-pressure impactor, the detector can be used to produce the particle size distribution of FIG. 5, in which the aerodynamic particle size is indicated on the horizontal axis and the quantity of detected particles is indicated on the vertical axis. If the first detector is not operating but the flow to be analyzed is guided to the detector for measuring the particle size distribution, the distribution according to the envelope curve 51 indicated by a solid line in FIG. 5 is obtained.

When the first detector 21 in FIG. 2 or the mobility detector 41 in FIG. 4 is started, the quantity of particles shown by the area limited by the dotted line 52 is removed from the particle size distribution detected by the second detector. Thus, the second detector will detect the distribution according to the broken line 53.

As stated above, it will not be necessary that either of the used detectors is capable of the actual computing of the particle size distribution. It will be sufficient that the detectors produce a parameter relating to the particle distribution, to be used in the computation of the desired property. In such a situation, the first detector could produce a signal which is proportional to the particle distribution detected by the first detector. For example, the first detector could produce a current signal which is proportional to the area hatched with vertical lines and remaining below the dotted curve 52 in FIG. 5. Furthermore, the second detector could produce a current signal which is proportional to the area hatched with horizontal lines and remaining below the broken line in FIG. 5.

In another embodiment, at least one of the measured parameters relating to the particle distribution contains information about at least the shape of the particle distribution measured at the second measuring point. Such parameters include standard deviation or, for example, the above-described median aerodynamic and mobility sizes.

By means of the invention described above, the properties of the particle distribution contained in the particle flow can be measured simultaneously at a large range of particle sizes. The present invention thus eliminates the need of so-called scanning measurement according to prior art, by replacing the classification step of prior art with the measuring step. This will make real-time measurement possible.

Hereinabove, some embodiments of the method and device according to the invention have been described; however, the invention is not restricted solely to these embodiments, but it can vary within the scope of the appended claims. In particular, it has been described above that the first detector is a mobility analyzer and the second detector is an electrical low-pressure impactor. However, this arrangement is only presented as an example and it is intended to elucidate the principle of operation of the invention. In practice, under some conditions, it may be advantageous for example that the detectors are in a different order; thus, it is advantageously possible to measure the parameter relating to the aerodynamic size of the particles at the first measuring point and the parameter relating to the mobility of the particles at the second point.

The invention claimed is:

1. A method for measuring properties of a particle distribution, the method comprising:
    guiding a particle flow to be analyzed to a first measuring point;
    detecting particles at the first measuring point;
    producing a parameter relating to a mobility of the particles and being proportional to the detected particles;

leading at least part of the flow that has passed through the first measuring point to a second measuring point;

measuring at the second measuring point a parameter relating to an aerodynamic size of the particles; and utilizing said parameter relating to the mobility and said parameter relating to the aerodynamic size to determine at least one property of the particle distribution of the particle flow.

2. The method according to claim 1, wherein the method is carried out in real time.

3. The method according to claim 1, further comprising: restricting access of particles detected at the first measuring point to the second measuring point.

4. The method according to claim 3, wherein access of particles detected at the first measuring point to the second measuring point is restricted by using a collecting method of measuring at the first measuring point.

5. The method according to claim 1, further comprising: computing at least an effective density of the particle distribution contained in the particle flow.

6. The method according to claim 1, wherein said parameter relating to the mobility is measured by means of a mobility channel detector.

7. The method according to claim 1, wherein said parameter relating to the mobility relates to an electrical mobility of particles.

8. The method according to claim 1, wherein said parameter relating to the mobility relates to a mechanical mobility of particles.

9. The method according to claim 1, wherein said parameter relating to the particle size is measured by means of an electrical low-pressure impactor.

10. The method according to claim 1, wherein at least one of said parameters contains information about a shape of at least one of the measured particle distributions.

11. The method according to claim 1, further comprising: utilizing said parameter relating to the mobility of the particles to determine a median particle size in relation to a mobility size.

12. The method according to claim 1, further comprising: utilizing said parameter relating to the aerodynamic size of the particles to determine a median particle size in relation to the aerodynamic size.

13. The method according to claim 1, further comprising: utilizing said parameter relating to the aerodynamic size of the particles to determine a particle size distribution in relation to the aerodynamic size.

14. A method for measuring properties of a particle distribution, the method comprising:

guiding a particle flow to be analyzed to a first measuring point;

measuring at the first measuring point a parameter relating to an aerodynamic size of the particles;

leading at least part of the flow that has passed the first measuring point to a second measuring point;

detecting particles at the second measuring point;

producing a parameter relating to a mobility of the particles and being proportional to the detected particles; and utilizing said parameter relating to the mobility and said parameter relating to the aerodynamic size to determine at least one property of the particle distribution of the particle flow.

15. A device for measuring properties of a particle distribution, comprising:

means for detecting particles at a first or a second measuring point;

means for producing a parameter relating to a mobility of particles based on detected particles;

means for measuring a parameter relating to an aerodynamic size of the particles at the first or the second measuring point; and means for computing at least one property of the original particle distribution by means of said parameter relating to the mobility of the particles and said parameter relating to the aerodynamic size.

16. The device according to claim 15, wherein said means for measuring the parameter relating to the mobility of the particle comprises a mobility detector.

17. The device according to claim 15, wherein said means for measuring the parameter relating to the aerodynamic size of the particle comprises an electrical low-pressure impactor.

* * * * *